(12) United States Patent
Zhu et al.

(10) Patent No.: US 7,177,681 B2
(45) Date of Patent: *Feb. 13, 2007

(54) CARDIAC RHYTHM MANAGEMENT SYSTEM FOR EDEMA

(75) Inventors: Qingsheng Zhu, Little Canada, MN (US); Julio C. Spinelli, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 503 days.

This patent is subject to a terminal disclaimer.

(21) Appl. No.: 10/411,795

(22) Filed: Apr. 11, 2003

(65) Prior Publication Data

US 2003/0191503 A1 Oct. 9, 2003

Related U.S. Application Data

(63) Continuation of application No. 09/919,483, filed on Jul. 31, 2001.

(51) Int. Cl.
*A61N 1/365* (2006.01)
(52) U.S. Cl. .......................................... 607/9; 607/17
(58) Field of Classification Search .............. 607/5–25; 600/547
See application file for complete search history.

(56) References Cited

U.S. PATENT DOCUMENTS

| | | | |
|---|---|---|---|
| 3,340,867 A | 9/1967 | Kubicek et al. | |
| 3,871,359 A | 3/1975 | Pacela | |
| 4,003,379 A | 1/1977 | Ellinwood, Jr. | 128/260 |
| 4,059,169 A | 11/1977 | Hagen | |
| RE30,101 E | 9/1979 | Kubicek et al. | |
| 4,271,192 A | 6/1981 | Wurtman et al. | 424/319 |
| 4,437,469 A | 3/1984 | Djordjevich et al. | |
| 4,450,527 A | 5/1984 | Sramek | |
| 4,470,987 A | 9/1984 | Wurtman et al. | 424/259 |
| 4,472,420 A | 9/1984 | Toth | |
| 4,472,431 A | 9/1984 | Toth | |
| 4,559,946 A | 12/1985 | Mower | 128/419 D |
| 4,562,843 A | 1/1986 | Djordjevich et al. | |
| 4,567,892 A | 2/1986 | Plicchi et al. | |
| 4,576,183 A | 3/1986 | Plicchi et al. | 600/536 |
| 4,651,716 A | 3/1987 | Forester et al. | 128/1 D |
| 4,693,253 A | 9/1987 | Adams | 128/419 D |
| 4,880,005 A | 11/1989 | Pless et al. | 128/418 PG |

(Continued)

FOREIGN PATENT DOCUMENTS

EP 348271 12/1989

(Continued)

OTHER PUBLICATIONS

Spinelli, J.C., et al., "Method and System for Treatment of Neurocardiogenic Syncore", U.S. Appl. No. 10/862,631, filed Jun. 7, 2004, 15 pages.

(Continued)

*Primary Examiner*—Scott M. Getzow
(74) *Attorney, Agent, or Firm*—Schwegman, Lundberg, Woessner, & Kluth

(57) ABSTRACT

A cardiac rhythm management system detects edema. In response to an episode of detected edema, it initiates or adjusts a cardiac resynchronization therapy and/or a cardiac contractility modulation (CCM) therapy.

118 Claims, 8 Drawing Sheets

U.S. PATENT DOCUMENTS

| | | | |
|---|---|---|---|
| 4,884,576 A | 12/1989 | Alt | 128/419 PG |
| 4,904,472 A | 2/1990 | Belardinelli et al. | 514/263 |
| 4,919,136 A | 4/1990 | Alt | |
| 4,980,379 A | 12/1990 | Belardinelli et al. | 514/821 |
| 4,987,897 A | 1/1991 | Funke | 128/419 PG |
| 5,002,052 A | 3/1991 | Haluska | 128/419 PG |
| 5,003,976 A | 4/1991 | Alt | |
| 5,025,786 A | 6/1991 | Siegel | 600/375 |
| 5,031,629 A | 7/1991 | DeMarzo | |
| 5,113,869 A | 5/1992 | Nappholz et al. | 128/696 |
| 5,117,825 A | 6/1992 | Grevious | 128/419 PG |
| 5,178,154 A | 1/1993 | Ackmann et al. | |
| 5,179,947 A | 1/1993 | Meyerson et al. | |
| 5,199,428 A | 4/1993 | Obel et al. | 128/419 C |
| 5,213,098 A | 5/1993 | Bennett et al. | 128/419 |
| 5,215,083 A | 6/1993 | Drane et al. | 128/419 D |
| 5,233,985 A | 8/1993 | Hudrlik | 607/27 |
| 5,246,008 A | 9/1993 | Mueller | 600/508 |
| 5,271,395 A | 12/1993 | Wahlstrand et al. | 607/9 |
| 5,273,034 A | 12/1993 | Nilsson | |
| 5,282,836 A | 2/1994 | Kreyenhagen et al. | 607/4 |
| 5,282,840 A | 2/1994 | Hudrlik | 607/28 |
| 5,284,136 A | 2/1994 | Hauck et al. | 607/24 |
| 5,292,343 A | 3/1994 | Blanchette et al. | 607/32 |
| 5,300,093 A | 4/1994 | Koestner et al. | 607/32 |
| 5,309,917 A | 5/1994 | Wang et al. | |
| 5,313,953 A | 5/1994 | Yomtov et al. | 128/696 |
| 5,324,309 A | 6/1994 | Kallok | 607/5 |
| 5,324,315 A | 6/1994 | Grevious | 607/60 |
| 5,344,429 A | 9/1994 | Smits | 607/5 |
| 5,354,317 A | 10/1994 | Alt | 607/19 |
| 5,354,319 A | 10/1994 | Wyborny et al. | 128/904 |
| 5,355,894 A | 10/1994 | Sivard | |
| 5,366,485 A | 11/1994 | Kroll et al. | 607/5 |
| 5,370,665 A | 12/1994 | Hudrlik | 607/9 |
| 5,404,877 A | 4/1995 | Nolan et al. | |
| 5,405,362 A | 4/1995 | Kramer et al. | 607/5 |
| 5,411,031 A | 5/1995 | Yomtov | 128/706 |
| 5,431,682 A | 7/1995 | Hedberg | 607/5 |
| 5,441,525 A | 8/1995 | Shelton et al. | 607/23 |
| 5,443,073 A | 8/1995 | Wang et al. | |
| 5,454,377 A | 10/1995 | Dzwonczyk et al. | |
| 5,464,434 A | 11/1995 | Alt | 607/6 |
| 5,479,369 A | 12/1995 | Matsumura et al. | 365/189.05 |
| 5,501,701 A | 3/1996 | Markowitz et al. | 607/9 |
| 5,505,209 A | 4/1996 | Reining | |
| 5,507,785 A | 4/1996 | Deno | 607/24 |
| 5,522,860 A | 6/1996 | Molin et al. | |
| 5,526,808 A | 6/1996 | Kaminsky | |
| 5,534,018 A | 7/1996 | Wahlstrand et al. | 607/27 |
| 5,540,728 A | 7/1996 | Shelton et al. | 607/23 |
| 5,562,711 A | 10/1996 | Yerich et al. | 607/17 |
| 5,562,712 A | 10/1996 | Steinhaus et al. | |
| 5,626,623 A | 5/1997 | Kieval et al. | 607/23 |
| 5,642,734 A | 7/1997 | Ruben et al. | |
| 5,676,686 A | 10/1997 | Jensen et al. | 607/9 |
| 5,685,316 A | 11/1997 | Schookin et al. | |
| 5,706,829 A | 1/1998 | Kadri | 128/898 |
| 5,722,999 A | 3/1998 | Snell | |
| 5,725,561 A | 3/1998 | Stroebel et al. | 607/9 |
| 5,725,562 A | 3/1998 | Sheldon | 607/19 |
| 5,732,710 A | 3/1998 | Rabinovich et al. | 600/547 |
| 5,749,369 A | 5/1998 | Rabinovich et al. | 600/547 |
| 5,749,900 A | 5/1998 | Schroeppel et al. | 607/4 |
| 5,782,774 A | 7/1998 | Shmulewitz | |
| 5,782,879 A | 7/1998 | Rosborough et al. | 607/6 |
| 5,782,884 A | 7/1998 | Stotts et al. | |
| 5,788,643 A | 8/1998 | Feldman | 600/506 |
| 5,791,349 A | 8/1998 | Shmulewitz | |
| 5,800,464 A | 9/1998 | Kieval | 607/9 |
| 5,865,760 A | 2/1999 | Lidman et al. | |
| 5,874,420 A | 2/1999 | Pelleg | 514/81 |
| 5,876,353 A | 3/1999 | Riff | 600/547 |
| 5,913,879 A | 6/1999 | Ferek-Petric et al. | 607/14 |
| 5,919,210 A | 7/1999 | Lurie et al. | 607/3 |
| 5,957,861 A | 9/1999 | Combs et al. | 600/547 |
| 5,957,957 A | 9/1999 | Sheldon | 607/17 |
| 5,978,705 A | 11/1999 | KenKnight et al. | 607/5 |
| 6,026,324 A | 2/2000 | Carlson | 607/27 |
| 6,035,233 A | 3/2000 | Schroeppel et al. | 600/515 |
| 6,044,297 A | 3/2000 | Sheldon et al. | 607/17 |
| 6,049,735 A | 4/2000 | Hartley et al. | 607/9 |
| 6,075,015 A | 6/2000 | Sestelo et al. | |
| 6,076,015 A | 6/2000 | Hartley et al. | 607/20 |
| 6,078,834 A | 6/2000 | Lurie et al. | 607/3 |
| 6,095,987 A | 8/2000 | Shmulewitz et al. | |
| 6,104,949 A | 8/2000 | Pitts Crick et al. | 600/547 |
| 6,154,672 A | 11/2000 | Pendekanti et al. | 607/5 |
| 6,161,038 A | 12/2000 | Schookin et al. | |
| 6,186,955 B1 | 2/2001 | Baura | |
| 6,228,033 B1 | 5/2001 | Koobi et al. | |
| 6,292,689 B1 | 9/2001 | Wallace et al. | |
| 6,298,267 B1 | 10/2001 | Rosborough et al. | 607/6 |
| 6,317,631 B1 | 11/2001 | Ben-Haim et al. | 607/9 |
| 6,336,903 B1 | 1/2002 | Bardy | |
| 6,411,844 B1 | 6/2002 | Kroll et al. | 607/5 |
| 6,438,408 B1 | 8/2002 | Mulligan et al. | |
| 6,473,640 B1 | 10/2002 | Erlebacher | 600/547 |
| 6,511,438 B2 | 1/2003 | Bernstein et al. | |
| 6,512,949 B1 | 1/2003 | Combs et al. | 600/547 |
| 6,560,481 B1 | 5/2003 | Heethaar et al. | |
| 6,561,986 B2 | 5/2003 | Baura et al. | |
| 6,595,927 B2 | 7/2003 | Pitts-Crick et al. | |
| 6,600,949 B1 | 7/2003 | Turcott | |
| 6,602,201 B1 | 8/2003 | Hepp | |
| 6,625,492 B2 | 9/2003 | Florio et al. | 607/17 |
| 6,636,754 B1 | 10/2003 | Baura et al. | |
| 6,643,543 B2 | 11/2003 | Takehara et al. | |
| 6,714,813 B2 | 3/2004 | Ishigooka et al. | |
| 6,748,271 B2 | 6/2004 | Spinelli et al. | 607/9 |
| 6,752,765 B1 | 6/2004 | Jensen et al. | |
| 6,811,537 B2 | 11/2004 | Bardy | |
| 6,829,503 B2 | 12/2004 | Alt | |
| 6,907,288 B2 | 6/2005 | Daum | |
| 6,908,437 B2 | 6/2005 | Bardy | |
| 6,912,420 B2 | 6/2005 | Scheiner et al. | |
| 2001/0020138 A1 | 9/2001 | Ishigooka et al. | |
| 2002/0115939 A1 | 8/2002 | Mulligan et al. | |
| 2002/0123674 A1 | 9/2002 | Plicchi et al. | |
| 2002/0138014 A1 | 9/2002 | Baura et al. | |
| 2002/0147475 A1 | 10/2002 | Schneiner et al. | 607/17 |
| 2002/0147476 A1 | 10/2002 | Daum | 607/17 |
| 2002/0193689 A1 | 12/2002 | Bernstein et al. | |
| 2003/0028221 A1 | 2/2003 | Zhu et al. | 607/9 |
| 2003/0055461 A1 | 3/2003 | Girouard et al. | |
| 2003/0074029 A1 | 4/2003 | Deno et al. | |
| 2003/0105496 A1 | 6/2003 | Yu et al. | |
| 2003/0176896 A1 | 9/2003 | Lincoln et al. | |
| 2003/0191503 A1 | 10/2003 | Zhu et al. | |
| 2003/0220580 A1 | 11/2003 | Alt | |
| 2004/0049235 A1 | 3/2004 | Deno et al. | |
| 2004/0073128 A1 | 4/2004 | Hatlestad et al. | |
| 2004/0102712 A1 | 5/2004 | Belalcazar et al. | |
| 2004/0116819 A1 | 6/2004 | Alt | |
| 2004/0133079 A1 | 7/2004 | Mazar et al. | |
| 2004/0147982 A1 | 7/2004 | Bardy | |
| 2004/0172080 A1 | 9/2004 | Stadler et al. | |
| 2004/0215097 A1 | 10/2004 | Wang | |
| 2004/0215270 A1 | 10/2004 | Ritscher et al. | |
| 2005/0004609 A1 | 1/2005 | Stahmann et al. | |
| 2005/0021098 A1 | 1/2005 | Spinelli et al. | |
| 2005/0080460 A1 | 4/2005 | Wang et al. | |
| 2005/0137480 A1 | 6/2005 | Alt et al. | |
| 2005/0283197 A1 | 12/2005 | Daum et al. | |

| | | | |
|---|---|---|---|
| 2006/0041280 | A1 | 2/2006 | Stahmann et al. |

FOREIGN PATENT DOCUMENTS

| | | |
|---|---|---|
| EP | 0584388 A1 | 3/1994 |
| EP | 0620420 | 10/1994 |
| EP | 0663219 A1 | 7/1995 |
| EP | 1057498 | 12/2000 |
| EP | 1078597 | 2/2001 |
| EP | 606301 | 12/2001 |
| EP | 1247487 | 10/2002 |
| EP | 1275342 | 1/2003 |
| EP | 771172 | 4/2003 |
| WO | WO-8400227 | 1/1984 |
| WO | WO-9304627 | 3/1993 |
| WO | WO-9601586 | 1/1996 |
| WO | WO-9737591 | 10/1997 |
| WO | WO-9738628 | 10/1997 |
| WO | WO-9851211 | 11/1998 |
| WO | WO-0141638 | 6/2001 |
| WO | WO-02053026 | 7/2002 |
| WO | WO-02053228 | 7/2002 |
| WO | WO-03020364 | 3/2003 |

OTHER PUBLICATIONS

Berman, I R., et al., "Transthoracic electrical impedance s a guide to intravascular overload", Arch Surg., 102(1), (Jan. 1971), 61-4.

Charach, Gideon, et al., "Transthoracic monitoring of the impedance of the right lung in patients with cardiogenic pulmonary edema", Crit Care Med., 29(6), (Jun. 2001), 1137-44.

Ellenbogen, Kenneth A., et al., "Clinical cardiac pacing", Philadelphia: Saunders, (1995), 219-233.

Kusumoto, F M., et al., "Medical Progress: Cardiac Pacing", New England Journal of Medicine, 334(2), (Jan. 11, 1996), 89-98.

Lau, C P., et al., "Rate-responsive pacing with a pacemaker that detects respitory rate (Biorate): clinical advantages and complications", Clin Cardiol., 11(5), (May 1988), 318-24.

Pomerantz, M, et al., "Transthoracic electrical impedance for the early detection of pulmonary edema", Surgery, 66(1), (Jul. 1969), 260-8.

Rosbrough, John P., et al., "Electrical Therapy for Pulseless Electrical Activity", NASPE, Apr. 2000, v. 23, No. 4, Part II, Abstract, (2000), 591.

Shoemaker, W.C., et al., "Multicenter trial of a new throacic electrical bioimpedance device for cardiac output estimation", Crit Care Med., 22(12), (Dec. 1994), 1907-12.

Yu, Cheuk-Man, et al., "Early warning of CHF hospitalization by intra-thoracic impedance measurement in CHF patients with pacemakers", Pacing and Clinical Electrophysiology, 24, (Apr. 2001), 19.

Luepker, R. V., et al., "Transthoracic Electrical Impedance: Quantitative Evaluation of a Non-Invasive Measure of Throacic Fluid Volume", American Heart Journal, vol. 85, No. 1, (Jan. 1973), 83-93.

Mai, J., et al., "Enhanced Rate Response Algorithm for Orthostatic Compensation Pacing", Pace, 23, Naspe Abstracts, Abstract No. 678, (Apr. 2000), p. 722.

Adamicza, A., et al., "Changes in transthoracic electrical impedance during endotoxemia in dogs", Acta Physiol Hung., 85(4), (1997-98), 291-302.

Adamicza, A., et al., "Investigation of the thoracic electrical impedance during endotoxemia in dogs", Act Chir Hung., 36(1-4), (1997), 1-3.

Alt, Eckhard, et al., "Control of Pacemaker Rate by Impedance-based Respitory Minute Ventalation*", Chest, 92(2), (Aug. 1987), 247-252.

Baarends, E. M., et al., "Body-water compartments measured by bio-electrical impedance spectroscopy in patients with chronic obstructive pulmonary disease", Clinical Nutrition, 17(1), (Feb. 1998), 15-22.

Belalcazar, Andres, et al., "Improved lung edema monitoring with coronary vein pacing leads", Pacing and Clinical Electrophysiology, 26(4 pt. II), Abstract 18, (Apr. 2003), 933.

Belalcazar, Andres, et al., "Improved lung edema monitoring with coronary vein pacing leads: a simulation study", Physiological Measurement, vol. 25, (2004), 475-487.

Bradbury, M. G., et al., "Assessment of the sensitivity of bioimpedance to volume changes in body water", Pediatr Nephrol., 9(3), (Jun. 1995), 337-40.

Campbell, J. H., et al., "Clinical applications of electrical impedance tomography in the monitoring of changes in intrathoracic fluid volumes", Physiol. Meas., vol. 15, (1994), A217-A222.

Campbell, J. H., et al., "Detection of changes in intrathoracic fluid in man using electrical impedance tomography", Clinical Science, vol. 87, (1994), 97-101.

Chiolero, R. L., et al., "Assessment of changes in body water by bioimpedance in acutely ill surgical patients", Intensive Care Medicine, 18(6), (1992), 322-6.

Daum, Douglas R., "Systems and Methods for Hypotension", U.S. Appl. No. 11/141,260, filed May 31, 2005, 51 pages.

Defaye, P., et al., "Automatic Recognition of Abnormal Respiratory Events During Sleep by a Pacemaker Transthoracic Impedance Sensor", Journal of Cardiovascular Electrophysiology, 15(9), (Sep. 2004), 1034-40.

Denniston, J. C. et al., "Factors Influencing the measurement of stroke volume by electrical impedance", Physiology (1372-1377), Abstract No. 1373,463.

Denniston, J. C., et al., "Measurement of pleural effusion by electrical impedance", Journal of Applied Physiology, 38(5), (May 1975), 851-7.

Ebert, T J., et al., "The use of thoracic impedance for determining thoracic blood volume changes in man", Aviat Space Environ Med., 57(1), (Jan. 1986), 49-53.

Ellenbogen, Kenneth A., et al., Clinical Cardiac Pacing, Philadelphia: Sauders, (1995), 22-23.

Fein, Alan, et al., "Evaluation of Transthoracic Electrical Impedance in the Diagnosis of Pulmonary Edema", Circulation, 60(5), (Nov. 1979), 1156-1160.

Foremean, B, et al., "Intra-thoracic impedance: a surrogate measure of thoracic fluid—fluid accumulation status trail (Fast)", Journal of Cardiac Failure, 10(4 Suppl), Abstract 251, (2004), S86.

Forro, M., et al., "Total body water and ECFV measured using bioelectrical impedance analysis and indicator dilution in horses", Journal of Applied Physiology, 89(2), (Aug. 2000), 663-71.

Frerichs, I., et al., "Electrical impedance tomography in monitoring experimental lung injury", Intensive Care Med., 24(8), (Aug. 1998), 829-36.

Garland, J. S., et al., "Measurement of extravascular lung water in hemodialysis patients using blood ultrasound velocity and optical density dilution", ASAIO Journal 2002 48(4), (Jul.-Aug. 2002), 398-403.

Goovaerts, H. G., et al., "Microprocessor-based system for measurement of electrical impedances during haemodialysis and in postoperative care", Medical & Biological Engineering & Computing, vol. 26, (Jan. 1988), 75-80.

Gotshall, R W., et al., "Bioelectric impedance as an idex of thoracic fluid", Aviation Space and Environmental Medicine, 70(1), (Jan. 1999), 58-61.

Grimbert, F., et al., "Pulmonary water and thoracic impedance. Evaluation of a measurement technic", Annales de L'anesthésiologie Française, 16 Spec No. 2-3, French, (19975), 157-63.

Harris, N. D., et al., "Applications of applied potential tomography (APT) in respiratory medicine", Clinical Physics and Physiological Measurement, 8 Suppl A, (1987), 155-65.

Hoon, Raghunath S., et al., "Changes in Transthoracic electrical impedance at high altitude", British Heart Journal, vol. 39, (1997), 61-66.

Hull, E. T., et al., "The Transthoracic Impedance Method for the Determination of the Degree and Change in Extravascular Water", Acta Tuberc. Pneumol. Belg., 68(4), (1997), 369-377.

Hull, E. T., et al., "Transthoracic electrical impedance: artifacts associated with electrode movement", Resuscitation, 6(2), (1978), 115-124.

Ishibe, Y., et al., "Transthoracic electrical impedance method for measurement of pulmonary edema in vivo", Masui; 27(13), Japanese, (Dec. 1978), 1559-67.

Joekes, A. M., et al., "Impedance Cardiography—Its value in an intensive care unit", D) Materiels et techniques/Cardiocirculatory Equipment and Technics, Abstract No. 141, 1 Page.

Keller, Guido, et al., "Monitoring of Pulmonary Fluid Volume and Stroke Volume by Impedance Cardiography in Patients on Hemodialysis", Chest, 72(1), (Jul. 1977), 56-62.

Khan, Mahfooz R., et al., "Quantitative electrical-impedance plethysmopgraphy for pulmonary oedema", Medical & Biological Engineering & Computing, vol. 15, (Nov. 1977), 627-633.

Kiesler, T. W., et al., "Impedance cardiography by use of a spot-electrode array to track changes in cardiac output in anesthetized dogs.", Journal of the American Veterinary Medical Association, 196(11), (Jun. 1, 1990), 1804-10.

Koizumi, T., "Changes of transthoracic impedance (zinf 0 and deltaz) in newborn infants", Acta Neonatol. Jpn., 14(3), (1978), 335-340.

Kunst, P.W., et al., "Electrical impedance tomography in the assessment of extravascular lung water in noncardiogenic acute respiratory failure", Chest, 116(6), (Dec. 1999), 1695-702.

Larsen, F., et al., "Influence of furosemide and body posture on transthoracic electrical impedance in AMI", Chest, 90(5), (733-7), Nov. 1986.

Lau, C. P.., "The range of sensors and algorithms used in rate adaptive cardiac pacing", Pacing and clinical electrophysiology; PACE, 15(8), (Aug. 1992), 1177-211.

Leung, Zoe K., et al., "Feasability of an automatic atrial and ventricular threshold determination using thransthoracic using impedance", Pacing and Clinical Electrophysiology, vol. 19, Part II, Abstract 263, (Apr. 1996), 631.

McCarty, Richard N., et al., "Assessment of pulmonary edema in acute congestive heart failure with impedance cardiography", J Am Osteopath Assoc., 74(9), (May 1975), 879.

McNamee, James E., et al., "Peribronchial electrical admittance measures lung edema and congestion in the dog", Special Communications, Electrical Admittance and Pulmonary Edema, 337-341.

Newell, J. C., et al., "Assessment of acute pulmonary edema in dogs by electrical impedance imaging", IEEE Transactions on Biomedical Engineering, 43(2), (Feb. 1996), 133-138.

Nierman, D. M., et al., "Evaluation of transthoracic bioelectrical impedance analysis in monitoring lung water during diuresis", Applied Cardiopulmonary Pathophysiology, 7(1), (1997), 57-62.

Nierman, David M., et al., "Transthoracic Bioimpedance Can Messure Extravascular Lung Water in Acute Lung Injury1", Journal of Surgical Research 65, Article No. 0350, (1996), 101-108.

Noble, T. J., et al., "Diuretic induced change in lung water assessed by electrical impedance tomography", Physiol Meas., 21(1), (Feb. 2000), 155-63.

Nukiwa, Toshihiro, et al., "Responses of Serum and Lung Angiotensin-Converting Enzyme Activities in the Early Phase of Pulmonary Damage Induced by Oleic Acid in Dogs", Am Rev Respir Dis., 126(6), (Dec. 1982), 1080-1086.

Petersen, M E., et al., "Cardiac pacing for vasovagal syncope: a reasonable therapeutic option?", Pacing Clin Electrophysiol., 20(3 Pt 2), (Mar. 1997), 824-6.

Petersen, J. R., et al., "Electrical impedance measured changes in thoracic fluid content during thoracentesis", Clin Physiol., 14(4), (Jul 1994), 459-66.

Platia, Edward V., et al., "Time Course of Transvenous Pacemaker Stimulation Impedance, Capture Threshold, and Electrogram Amplitude", Pacing Clin Electrophysiol., 9(5), (Sep./Oct. 19), 620-625.

Raaijmakers, E., et al., "Estimation of non-cardiogenic pulmonary oedema using dual-frequency electrical impedance.", Medical & Biological Engineering & Computing, 36(4), (Jul. 1998), 461-6.

Raggueneau, J. L., et al., "Monitoring of intracellular and extracellular hydric compartments by body impedance", Anesth Anal. Rean, vol. 36, (1979), 439-443.

Ramos, Marcos U., et al., "Transthoracic electric impedance. A clinical guide of pulmonary fluid accumulation in congestive heart failure", Minnesota Medicine, 58(9), (Sep. 1975), 671-676.

Saunders, Charles E., "The Use of Transthoracic Electrical Bioimpedance in Assessing Thoracic Fluid Status in Emergency Department Patients", American Journal of Emergency Medicine, 6(4), (Jul. 1988), 337-340.

Schuster, C. J., et al., "Application of Impedance Cardiography in Critical Care Medicine", Resuscitation, vol. 11, (1984), 255-274.

Schwartzman, David, et al., "Serial Defibrillation Lead Impedance in Patients with Epicardial and Nonthoracotomy Lead Systems", Journal of Cardiovascular Electrophysiology, 7(8), (Aug. 1996), 697-703.

Shochat, M., et al., "Internal thoracic impedance monitoring: a new prospect in acute heart failure", European Heart Journal, 25(Supp), (Aug.-Sep. 2004), P72-2.

Smith, R. M., et al., "Canine thoracic electrical impedance with changes in pulmonary gas and blood volumes.", Journal of Applied Physiology , 53(6), (Dec. 1982), 1608-13.

Spinale, F. G., et al., "Noninvasive estimation of extravascular lung water using bioimpedance.", The Journal of Surgical Research, 47(6), (Dec. 1989), 535-40.

SRA, J S., et al., "Cardiac pacing during neurocardiogenic (vasovagal) syncope", J Cardiovasc Electrophysiol., 6(9), (Sep. 1995), 751-60.

Stadler, R., et al., "Automated detection of decreases in intrathoracic impredance to predict CHF hospitalization", Abstract 263, 26(4 pt II), Abstract 16, (Apr. 2003), 932.

Stahmann, Jeffrey, "Thoracic Impedance Detection With Blood Resistivity Compensation", U.S. Appl. No. 10/921,503, filed Aug. 19, 2004, 38 pgs.

Staub, N. C., "The measurement of lung water content.", The Journal of Microwave Power, 18(3), (Sep. 1983), 259-63.

Tang, W., "Assesment of total body water using bioelectrical impedance analysis in neonates receiving intensive care", Arch Dis Child Fetal Neonatal Ed., 77(2), (Sep. 1997), F123-6.

Tempel, G., et al., "Transthoracic electrical impedance in anaesthesia and intensive care.", Resuscitation, 6(2), (1978), 97-105.

Thakur, Ranjan K., et al., "Pericardial Effusion Increases Defibrillation Energy Requirement", Pacing Clin Electrophysiol., 16(6), (Jun. 1993), 1227-1230.

Vainshtein, G. B., et al., "The Functioning of the Cerebral Circulation System in Hyperthermia in Rabbits", Fiziol Zh SSSR Im I M Sechenova, 75(11), (Nov. 1989), 1608-1614.

Van De Water, Joseph M., et al., "Monitoring the Chest with Impedance", Chest, 64(5), (Nov. 1973), 597-603.

Wang, L., et al., "Impedance based prediction of CHF admission precedes symptoms in heart failure patients", Heartrhythm : the official journal of the Heart Rhythm Society, 1(Suppl 1), Abstract 679, (2004), S213.

Wang, Li, et al., "Multiple Sources of the Impedance Cardiogram Based on 3-D Finite Difference Human Thorax Models", IEEE Transactions on Biomedical Engineering, 42(2), (Feb. 1995), 141-148.

Wang, L., et al., "Prediction of CHF hospitalization by ambulatory inthrathoracic impedance measurement in CHF patients is feasable using pacemaker or ICD lead systems", Pacing and Clinical Electrophysiology, 26(4 pt. II), Abstract 123, (Apr. 2003), 959.

Yu, C., et al., "Changes in device based thoracic impedance in decompensating congestive heart failure", Circulation, 104(17 supplement), Abstract 1994, (2001), II-419.

Yu, C. M., et al., "Correlation of device-based intra-thoracic impedance and patient fluid status during intravenous diuretic therapy in acute CHF", Euopean Heart Journal, 23(Abstract Supplement), (2002), 158.

Yu, C., et al., "Device-based intra-thoracic impedance correlates with fluid status and provides automaticed prediction of CHF hospitalization", Journal of Cardiac Failure, 10(4 Suppl), Abstract 354, (2004), S113.

Yu, C., et al., "Early warning of CHF hospitalization by intra-thoracic impedance measurement in CHF patients with pacemakers", Pacing and Clinical Electrophysiology: PACE, 24(4 pt II), Abstract 19, (2002), 527.

Yu, C. M., et al., "Impedance measurements from implanted devices provided automated prediction of CHF hospitalization", *European Heart Journal*, 25(Supp), (Aug.-Sep. 2004), P27-27.

Yu, C. M., et al., "Intrathoracic impedance: A surrogate measure of fluid retention and predictor of hospitalization in patients with heart failure", *Journal of the American College of Cardiology*, 41(6 Supplement A), Abstract 1206-70, (2003), 210A.

Zellner, J. L., et al., "Bioimpedance: a novel method for the determination of extravascular lung water.", *The Journal of Surgical Research*, 48(5), (May 1990), 454-9.

Zima, E., "Intracardiac impedance in biventricular electrode configuration for left ventricular volume monitoring", *European Heart Journal*, 25(Supp), (Aug.-Sep. 2004), P165-165.

"Medtronic Announces European Release Of Innovative InSync Sentry Cardiac Resynchronization Therapy Defibrillator", http://www.medtronic.com/newsroom/news_20040614a.html, (2004), 2 pgs.

"Medtronic: InSync 7298: Dual Chamber Implantable Cardioverter Defibrillator with Cardiac Resynchronization Therapy (VVE-DDR) and Opti-Vol Fluid Monitoring: Reference Manual", www.medtronic.com, 420 pgs.

Stahmann, Jeffrey E., et al., "Improved Sensitivity and Specificity of Pulmonary Edema Detection When Using Transthoracic Impedance", U.S. Appl. No. 11/126,723, date filed May 11, 2005, 64 pgs.

CARDIAC RHYTHM MANAGEMENT SYSTEM FOR EDEMA

CROSS-REFERENCE TO RELATED APPLICATION(S))

This application is a continuation of U.S. patent application Ser. No. 09/919,483, filed on Jul. 31, 2001, the specification of which is incorporated herein by reference.

This application is related to the following co-pending and commonly assigned patent applications: U.S. patent application Ser. No. 09/832,365 entitled "CARDIAC RHYTHM MANAGEMENT SYSTEM FOR HYPOTENSION," filed on Apr. 10, 2001; U.S. patent application Ser. No. 09/879,665 entitled CARDIAC RHYTHM MANAGEMENT SYSTEM ADJUSTING RATE RESPONSE FACTOR FOR TREATING HYPTOTENSION, filed on Jun. 12, 2001; and to U.S. patent application Ser. No. 09/917,259 entitled "METHOD AND SYSTEM FOR TREATMENT OF NEUROCARDIOGENIC SYNCOPE," filed on Jul. 27, 2001, the specifications of which are incorporated herein by reference in their entirety.

TECHNICAL FIELD

This document relates generally to cardiac rhythm management systems and particularly, but not by way of limitation, to such a system for detecting and/or treating edema.

BACKGROUND

Excess fluid buildup ("edema") in a subject may be associated with many diseases. Edema results from inadequate or excessive response of homeostatic processes in the body. For example, acute pulmonary edema is a short-term fluid buildup in the lungs. In some people, such excess fluid buildup (also referred to as "decompensation") results from inadequate cardiac output of the heart, such as is associated with congestive heart failure ("CHF"). Pulmonary edema may occur late in the CHF disease process and, therefore, may have serious consequences. The fluid accumulation in the lungs may result in labored breathing and, in severe cases, may even result in death. For these and other reasons, there is a need to detect edema and, more importantly, to provide appropriate responsive therapy to treat edema and/or any underlying heart condition causing the edema.

SUMMARY

This document discusses a cardiac rhythm management system that detects edema. In response to an episode of detected edema, it initiates and/or adjusts a cardiac resynchronization therapy and/or a cardiac contractility modulation (CCM) therapy.

One example discusses a cardiac rhythm management system. The system includes an edema detection circuit to sense a condition correlative to edema in a subject. An electrical energy delivery circuit delivers electrical energy to the subject. A controller is coupled to the edema detection circuit to receive a detected edema indicator. The controller is also coupled to the energy delivery circuit to provide a control signal for timing delivery of the electrical energy to the subject. The controller includes a cardiac resynchronization therapy mode and a cardiac contractility modulation therapy mode. The controller is configured, in response to the detected edema indicator, to perform at least one of: initiating/adjusting the cardiac resynchronization therapy; and, initiating/adjusting the cardiac contractility modulation therapy. Other aspects of the invention will be apparent on reading the following detailed description of the invention and viewing the drawings that form a part thereof.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

Figure 1:
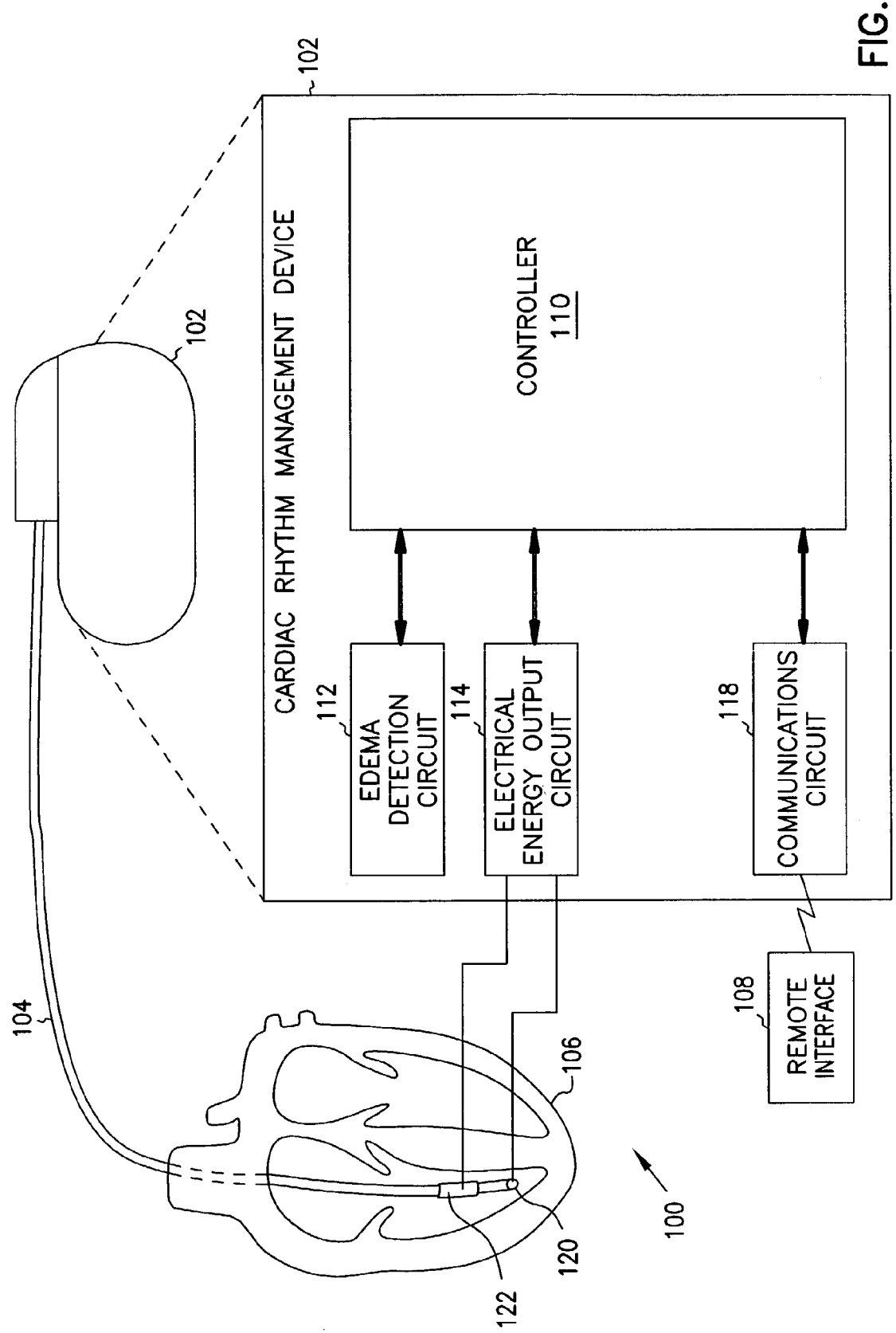
FIG. 1 is a block diagram example of portions of a cardiac rhythm management system and portions of an environment in which it is used.

FIG. 1 is a block diagram example of portions of one possible cardiac rhythm management system 100 and portions of an environment in which it is used. In this example, system 100 includes, among other things, a cardiac rhythm management device 102 and leadwire ("lead") 104. Leadwire 104 is coupled to device 102 for communicating one or more signals between device 102 and a portion of a living organism or other subject, such as heart 106. Some examples of device 102 include, among other things, bradycardia and antitachycardia pacemakers, cardioverters, defibrillators, combination pacemaker/defibrillators, cardiac resynchronization therapy devices, and drug delivery devices. Other examples of device 102 include any other implantable or external cardiac rhythm management apparatus capable of providing cardiac rhythm management therapy to heart 106. Such cardiac rhythm management therapy is not limited to managing cardiac rate. For example, cardiac rhythm management therapy also includes cardiac resynchronization therapy. Cardiac resynchronization therapy typically coordinates the spatial nature of a depolarization associated with a heart contraction in one or more heart chambers. While such cardiac resynchronization therapy may modify cardiac rate, it can also occur without any modification of the rate at which heart contractions occur. Some examples of cardiac resynchronization therapy include simultaneous or offset multichamber (e.g., biventricular) pacing and/or simultaneous or offset delivery of pacing pulses to multiple electrodes associated with a single heart chamber. Moreover, the cardiac rhythm management therapy discussed in this document also includes cardiac contractility modulation (CCM) therapy. CCM therapy includes delivering electrical energy to a portion of the heart during a refractory time period when that portion of the heart is relatively unlikely to contract in response to the received electrical energy. Therefore, CCM therapy need not adjust cardiac rate and, moreover, need not even evoke responsive heart contractions. System 100 may also include additional components such as, for example, an external or other remote interface 108 capable of communicating with device 102.

In this example, device 102 includes, among other things, a microprocessor or other controller 110 coupled to an edema detection circuit 112, an electrical energy output circuit 114, and a communication circuit 118. Communication circuit 118 is adapted for wireless or other communication with remote interface 108. Electrical energy output circuit 114 is coupled to one or more electrodes associated with any chamber(s) of heart 106, such as electrodes 120 and 122 of lead 104. Such electrodes deliver electrical pacing stimulations for evoking responsive heart contractions or for delivering cardiac contractility modulation ("CCM") energy pulses, which do not evoke responsive heart contractions, as discussed below.

In this example, edema detection circuit 112 detects a condition in the subject that is correlative to an episode of edema, and outputs a responsive edema indicator to controller 110. In one response to the detected edema, controller 110 initiates or adjusts a cardiac resynchronization therapy. In another response to the detected edema, controller 110 initiates or adjusts a CCM therapy. In a further example of operation, controller 110 communicates an indication of the detected edema through communication circuit 118 to remote interface 108 for visible display or for other user output.

Figure 2:
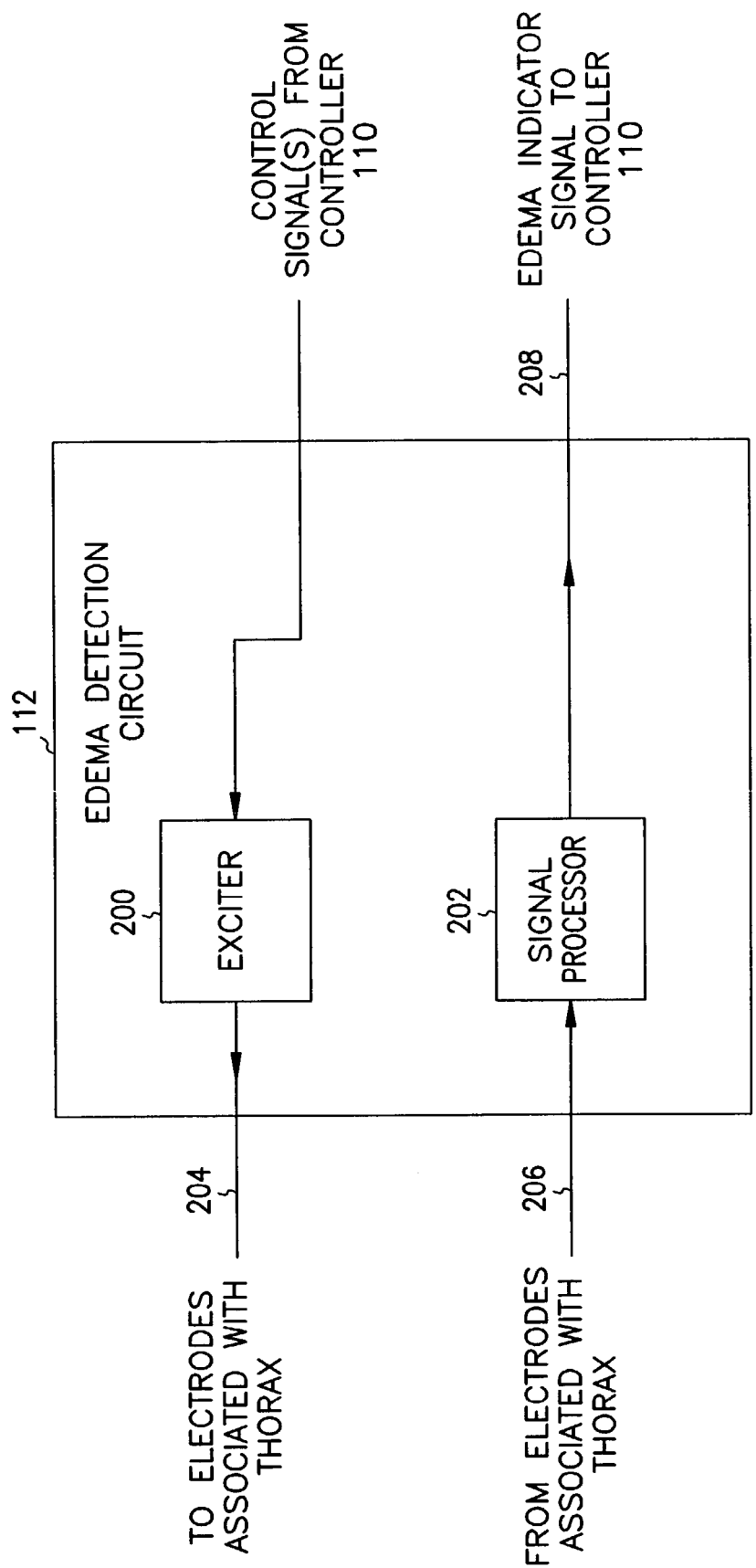
FIG. 2 is a block diagram example of one possible edema detection circuit.

FIG. 2 is a block diagram example of one possible edema detection circuit 112 that senses thoracic impedance to determine whether the edema condition is present. In this example, edema detection circuit includes exciter 200 and signal processor 202, both of which are coupled to electrodes associated with a portion of the subject's thorax. In this document, the term "thorax" refers to the subject's body other than the subject's head, arms, and legs. Exciter 200 provides, at node/bus 204, a test signal to the thorax, from which thoracic impedance is determined. Exciter 200 need not, and typically does not, stimulate tissue or muscle contractions in the thorax; it is referred to as an exciter because it provides a test excitation signal for determining impedance. Signal processor 202 receives from the thorax, at node/bus 206, signals responsive to the test signal provided by exciter 200. Signal processor 202 outputs, at node/bus 208, the edema indicator to controller 110.

The thoracic electrodes associated with exciter 200 may be different from the thoracic electrodes associated with signal processor 202. For example, one such suitable electrode configuration for sensing thoracic impedance includes the configuration of at least four electrodes for detecting thoracic impedance, such as discussed in Hauck et al. U.S. Pat. No. 5,284,136 entitled "DUAL INDIFFERENT ELECTRODE PACEMAKER," assigned to Cardiac Pacemakers, Inc., the disclosure of which is incorporated herein by reference in its entirety. However, a different number of electrodes (e.g., 2 or 3 electrodes, or more than 4 electrodes) could also be used. Therefore, in another example, one or more of the thoracic electrodes of edema detection circuit 112 is shared by both exciter 200 and signal processor 202.

In one example, exciter 200 and signal processor 202 cooperate to detect thoracic impedance using a high frequency carrier signal to provide the test stimulus that obtains the thoracic impedance response, as discussed in Hartley et al. U.S. Pat. No. 6,076,015 ("the Hartley et al. patent") entitled "RATE ADAPTIVE CARDIAC RHYTHM MANAGEMENT DEVICE USING TRANSTHORACIC IMPEDANCE," assigned to Cardiac Pacemakers, Inc., the disclosure of which is incorporated herein by reference in its entirety.

Figure 3:
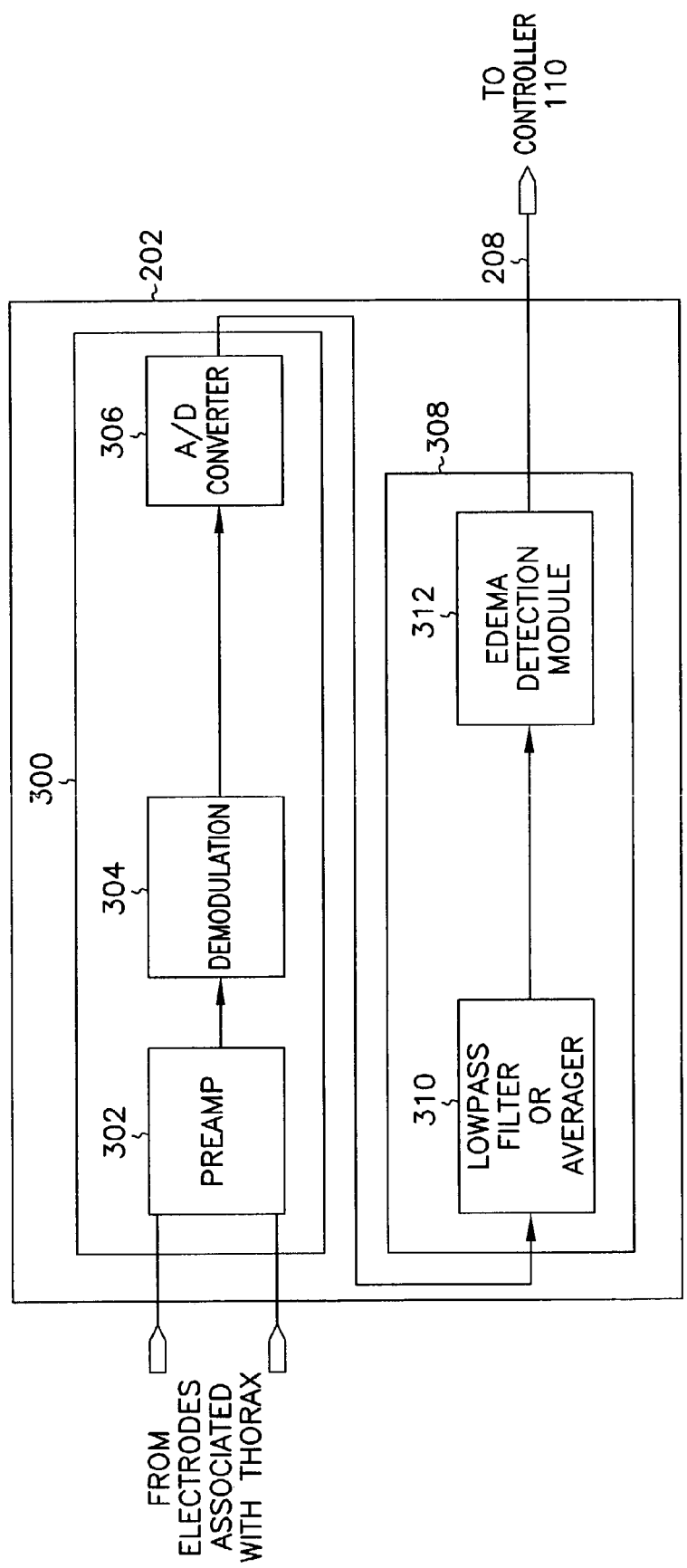
FIG. 3 is a block diagram example of portions of a possible signal processor.

FIG. 3 is a block diagram example of portions of a possible signal processor 202. The input signal from the thoracic electrodes, which is responsive to the test stimulus provided by exciter 200, is received by an analog signal processing circuit 300 at its preamplifier 302 circuit. A signal provided by an output of preamplifier 302 is received by a demodulator 304 circuit. Demodulator 304 demodulates the high frequency carrier signal to extract thoracic impedance information. A signal provided by an output of demodulator 304 is received by analog-to-digital (A/D) converter 306, where it is converted into a digital thoracic impedance signal. Suitable examples of preamplifier 302, demodulator 304, and A/D converter 306 are discussed in the Hartley et al. patent, which was above incorporated by reference in its entirety.

In this example, the digitized signal provided by A/D converter 306 undergoes further signal processing in the digital domain by digital signal processing circuit 308, which includes a lowpass filtering or averager 310 receiving the digital output signal from A/D converter 306. The digitized thoracic impedance signal is influenced not only by the amount of fluid in a subject's thorax, but also by the subject's heart beat (referred to as the "cardiac stroke" signal component) and the subject's breathing (also referred to as the "respiration" or "ventilation" component). Lowpass filter or averager 310 extracts the "dc" or "baseline" or "low frequency" component of the thoracic impedance signal (e.g., less than a cutoff value that is approximately between 0.1 Hz and 0.5 Hz, inclusive, such as, for example, a cutoff value of approximately 0.1 Hz). The baseline component of the thoracic impedance signal provides information about the amount of fluid in the subject's thorax. A decrease in the baseline thoracic impedance indicates the thoracic fluid accumulation condition associated with edema. In providing the baseline thoracic impedance output signal, lowpass filter or averager 310 attenuates the higher frequency components of the thoracic impedance signal that are influenced by the patient's breathing (e.g., approximately between 0.05 Hz and 2.0 Hz inclusive) and heartbeat (e.g., approximately between 0.5 Hz and 10 Hz inclusive). Digital signal processing circuit 308 also includes an edema detection module 312 which determines whether the baseline impedance signal received from lowpass filter or averager 310 indicates that edema is present in the subject, and provides the resulting edema indicator at node 208 to controller 110.

Figure 4:
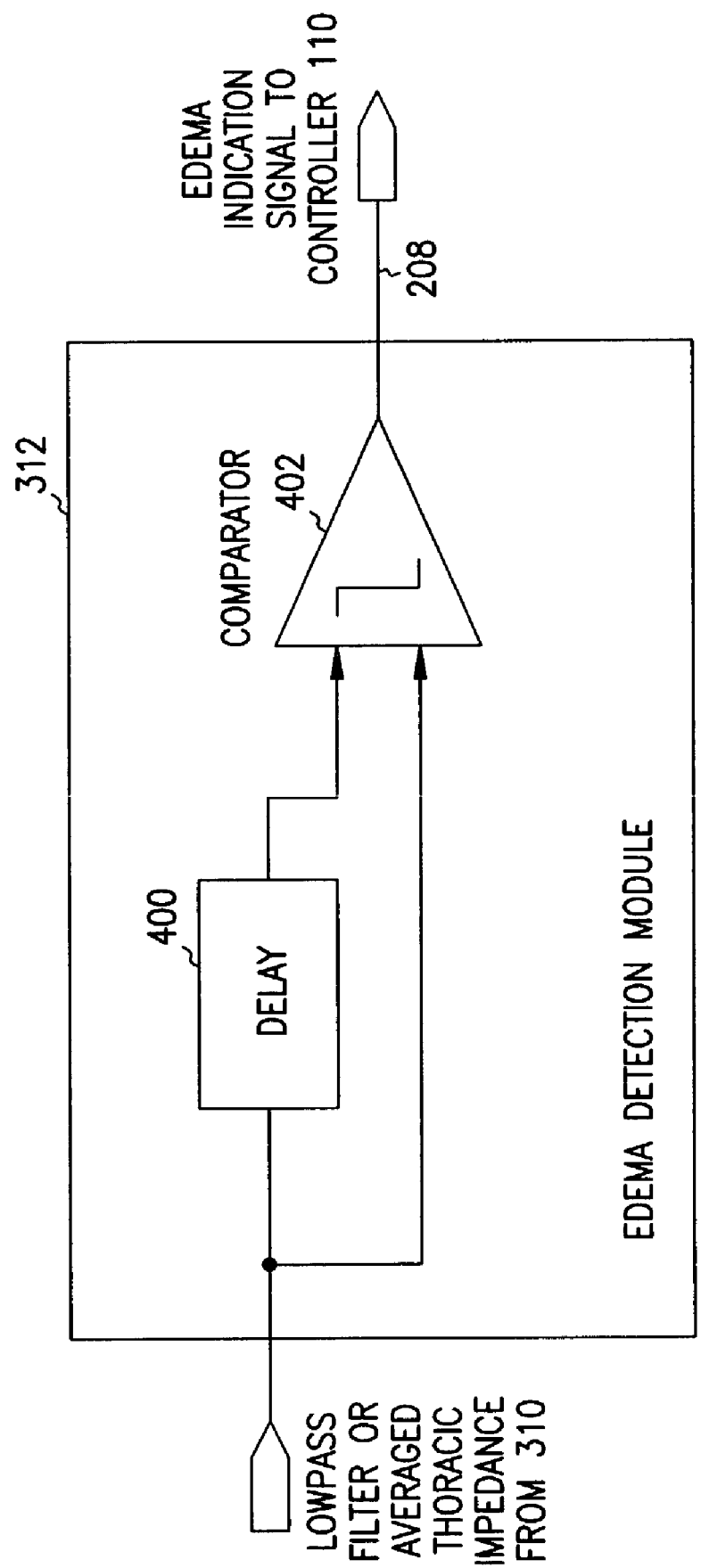
FIG. 4 is a block diagram example of one possible edema detection module.

FIG. 4 is a block diagram example of one possible edema detection module 312. It includes a delay 400 that outputs a long-term value of the lowpass-filtered thoracic impedance, that is, the baseline thoracic impedance including information about fluid shifts to and away from the thorax. Comparator 402 compares the substantially instantaneous and long-term values of the baseline thoracic impedance at its respective comparator inputs. If the substantially instantaneous baseline thoracic impedance is less than the long-term value of the baseline thoracic impedance by a predetermined threshold value, then comparator 402 provides a resulting signal, at node 208, that indicates that edema is present. Otherwise, the resulting signal at node 208 indicates that edema is not present.

Figure 5:
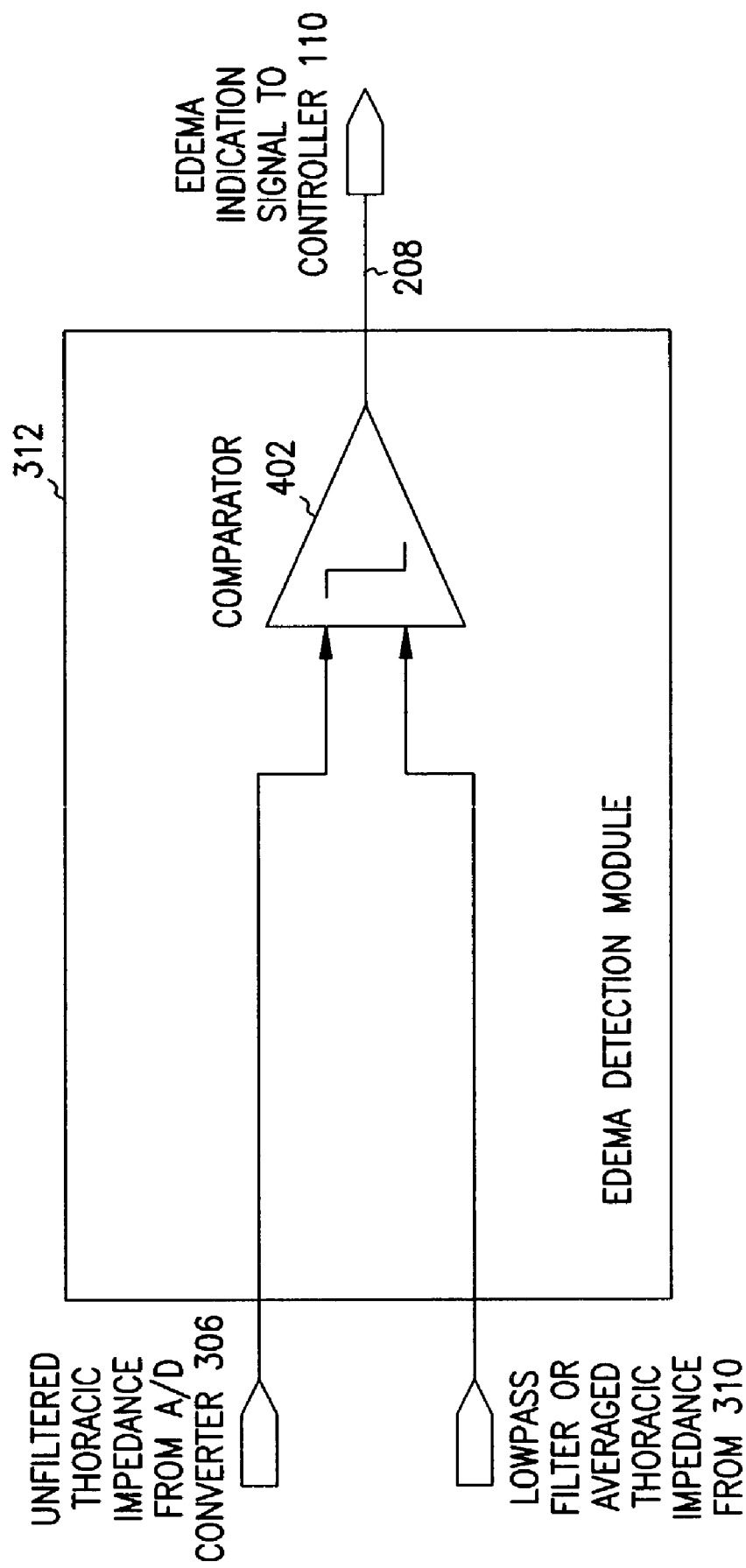
FIG. 5 is a block diagram example of an alternative edema detection module.

FIG. 5 is a block diagram example of an alternative edema detection module 312. In this example, comparator 402 compares the unfiltered thoracic impedance from the output A/D converter 306 to the lowpass-filtered thoracic impedance (i.e., the baseline thoracic impedance) from the output of lowpass filter or averager 310. If the unfiltered thoracic impedance from A/D converter 306 is less than the baseline thoracic impedance from lowpass filter or averager 310 by a predetermined threshold value, then comparator 402 provides the resulting signal, at node 208, that indicates that edema is present. Otherwise, the resulting signal at node 208 indicates that edema is not present.

Figure 6:
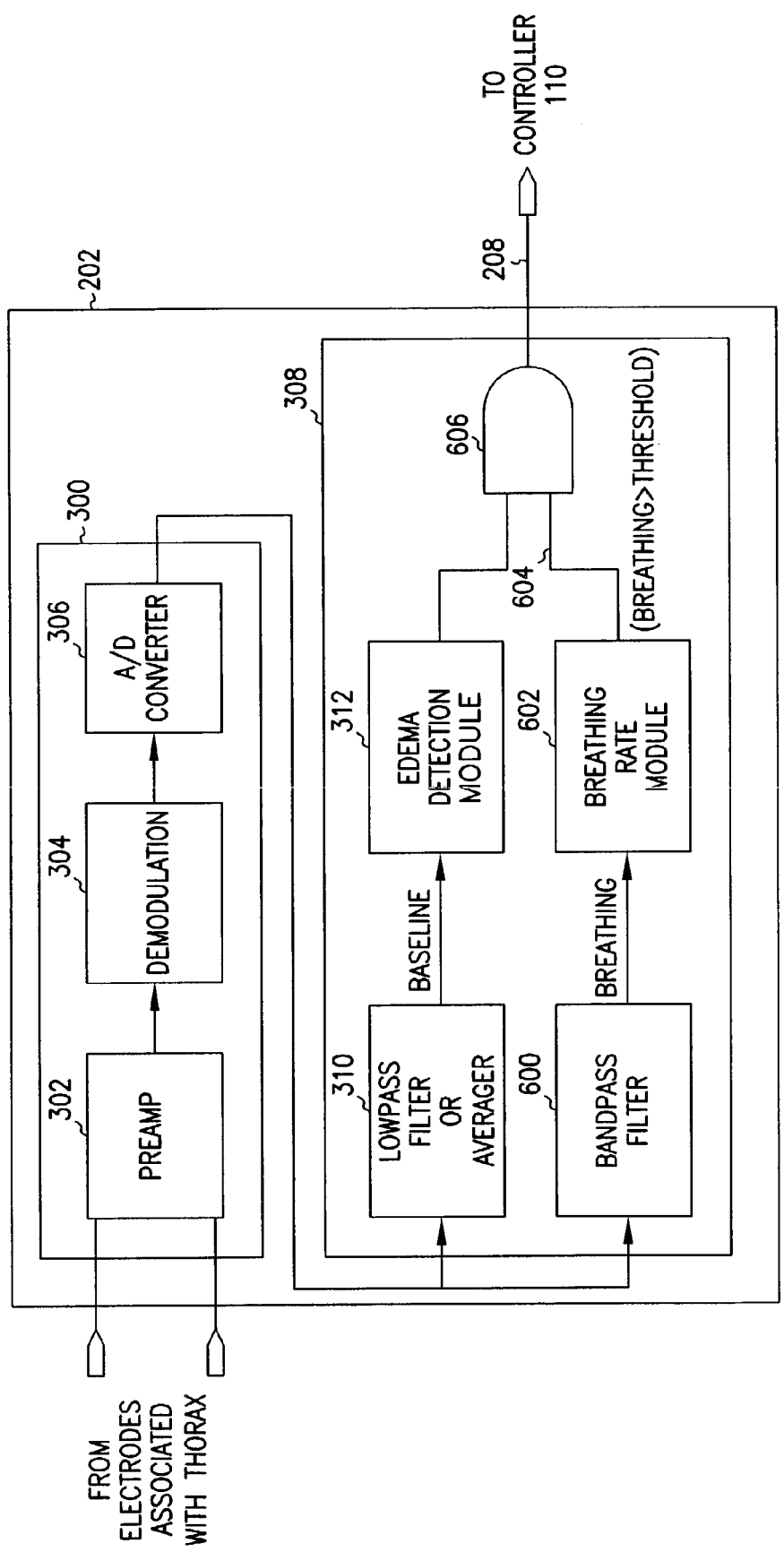
FIG. 6 is a block diagram example of an alternative signal processing circuit that determines whether edema is present based not only on the baseline thoracic impedance signal, but also on an additional breathing rate criterion.

FIG. 6 is a block diagram example of an alternative signal processing circuit 202 that determines whether edema is present based not only on the baseline thoracic impedance signal, but also on an additional breathing rate criterion. In the example of FIG. 6, the digitized thoracic impedance signal from A/D converter 306 is also received at an input of bandpass filter 600. Bandpass filter 600 attenuates frequencies outside the frequency range associated with the breathing component of the thoracic impedance signal (e.g., approximately between 0.05 Hz and 2.0 Hz inclusive). Bandpass filter 600 outputs a signal correlative to the subject's breathing, which is received at an input of breathing rate module 602. Breathing rate module 602 includes a fiducial point detector (e.g., zero-cross detector, level detector, peak detector, etc.) Dejection a fiducial point on the breathing signal that occurs a known number of one or more times during breathing cycle (of inhaling and exhaling). A timer measures the time interval between respective successive fiducial points, from which the breathing rate is determined. A comparator compares the breathing rate to a threshold value that is approximately between 10 breaths per minute and 40 breaths per minute, such as about 25 breaths per minute. Breathing rate module 602 outputs at node 604 a digital signal indicating whether the breathing rate threshold is being exceeded. This signal is used (e.g., by AND gate 606) to qualify the signal output from edema detection module 312. Therefore, the edema-present indicator at node 208 is asserted only if both the baseline thoracic impedance indicates a fluid accumulation in the thorax and the breathing rate exceeds the threshold value.

In a further example, in which device 102 includes an activity sensor (such as, for example, an accelerometer), the signal output from edema detection module 312 is further qualified by a digital signal indicating whether the patient is resting. This is determined by comparing the activity level indicated by the activity sensor to a threshold value. The patient is deemed to be resting when the activity level is less than the threshold value. In such an example, AND gate 606 is implemented as a 3-input AND gate, with a first input receiving the output of edema detection module 312, a second input receiving the output of breathing rate module 602, and a third input receiving a signal, based on the comparison of the activity level to the threshold value, that is a logical "1" if the patient is resting. The output of the 3-input AND gate is communicated, at node 208, to controller 110. In this example, the edema-present indicator at node 208 is asserted only if both the baseline thoracic impedance indicates a fluid accumulation in the thorax and the resting breathing rate exceeds the threshold value.

Figure 7:
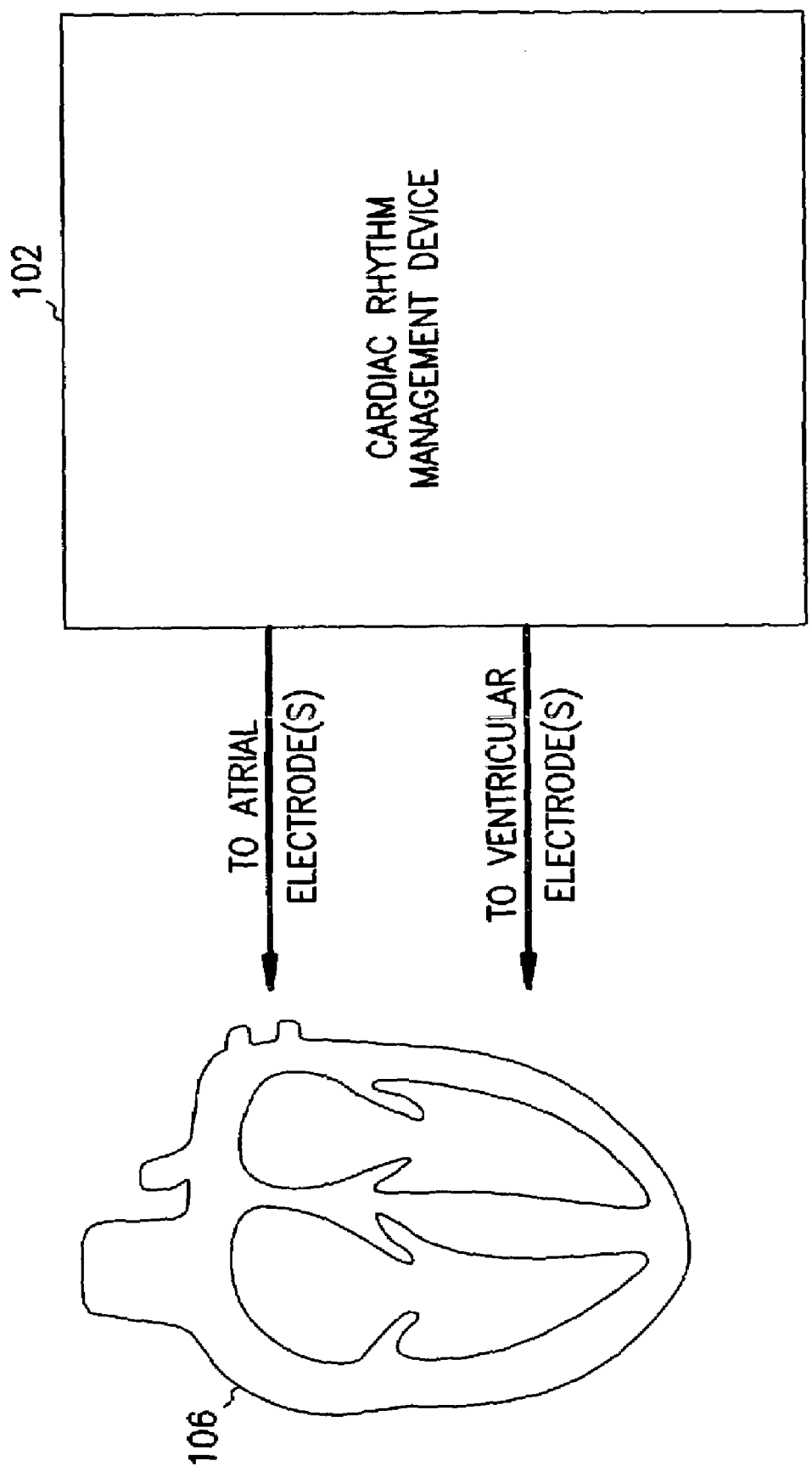
FIG. 7 is a block diagram example in which a cardiac rhythm management device is associated with a heart at both an atrium (right or left) and a ventricle (right or left).

When the edema indicator received at node 208 by controller 110 indicates that edema is present, controller 110 responds by initiating or adjusting a therapy provided to heart 106. In one example, controller 110 responds to an edema detection by initiating or adjusting a cardiac resynchronization therapy that coordinates the spatial nature of a depolarization associated with a heart contraction in one or more heart chambers. FIG. 7 is a block diagram example in which device 102 is associated with heart 106 at both an atrium (right or left) and a ventricle (right or left) for sensing and/or pacing atrial and/or ventricular heart contractions occurring during the same cardiac cycle (of an atrial and subsequent ventricular contraction). The atrial contraction and the subsequent ventricular contraction occurring during the same cardiac cycle are separated by a time interval that is referred to as an atrioventricular (AV) delay. In one example of adjusting a cardiac resynchronization therapy in response to detected edema, controller 110 adjusts the AV delay value stored in a memory location of controller 110. In one example, the AV delay value is programmable by the user to be approximately between 20 milliseconds and 200 milliseconds, such as about 100 milliseconds. In response to the detected edema, controller 110 incrementally adjusts, over a suitable period of time for allowing the edema to abate, the AV delay to a shorter or longer value until the edema abates or all possible AV delay values have been exhausted.

In an example of initiating a cardiac resynchronization therapy in response to the detected edema, controller 110 switches from pacing a single ventricle (e.g., the right ventricle) to biventricular pacing of electrodes associated with each of the right and left ventricles. One suitable electrode configuration for biventricular pacing includes at least one intravascular electrode in the right ventricle and at least one other intravascular electrode introduced into the coronary sinus and/or great cardiac vein into association with the left ventricle. The biventricular pacing includes simultaneous delivery of pacing stimuli to both ventricles. The biventricular pacing also includes delivering such pacing stimuli in different ventricles at different times that are separated by an interventricular delay.

In an example of adjusting a cardiac resynchronization therapy in response to the detected edema, such as when biventricular pacing therapy is already being provided, controller 110 adjusts the value of the interventricular delay. In one example, the interventricular delay value is programmable by the user to be approximately between 20 milliseconds and 200 milliseconds, such as about 100 milliseconds. In response to the detected edema, controller 110 incrementally adjusts, over a suitable period of time for allowing the edema to abate, the interventricular delay value to a shorter or longer value until the edema abates or all possible interventricular delay values have been exhausted.

In another example of adjusting a cardiac resynchronization therapy in response to the detected edema, such as when multiple electrodes are associated with a single heart chamber, is to select a different one of the same-chamber electrodes for providing the pacing stimulations associated with that heart chamber. One such possible electrode configuration includes two coronary sinus and/or great cardiac vein electrodes associated with the different locations of the left ventricle. In this example, the left ventricular electrodes are positioned for association with different locations in the left ventricle. For example, such left ventricular electrodes may be positioned in apical, midregion, and basal left ventricular locations. In this example, when left ventricular pacing therapy is being delivered from one of the left ventricular electrodes (with or without corresponding right ventricular pacing therapy), controller 110 responds to the detected edema by shifting to a different left ventricular electrode for providing pacing therapy. In a further example, when left ventricular pacing therapy is being delivered at more than one left ventricular electrode, controller 110 responds to an edema detection by adjusting an interelectrode delay between delivery of the pacing pulses at the different left ventricular electrodes. In one example, the interelectrode delay between delivery of the pacing pulses at the left ventricular electrodes is programmable by the user to values ranging approximately between −100 milliseconds and +100 milliseconds, such as about zero milliseconds. In response to the detected edema, controller 110 incrementally adjusts, over a suitable period of time for allowing the edema to abate, the interelectrode delay value to a shorter or longer value until the edema abates or all possible interelectrode delay values (or, for more than two same-chamber electrodes, all possible combinations of interelectrode delay values) have been exhausted.

In another example, controller 110 responds to an edema detection by initiating or adjusting cardiac contractility modulation (CCM) therapy, such as by using an excitable tissue controller (ETC). CCM therapy includes delivering electrical energy to a portion of the heart during a refractory time period when that portion of the heart is relatively unlikely to contract in response to the received electrical energy. Therefore, CCM therapy need not adjust cardiac rate and, moreover, need not even evoke responsive heart contractions. The electrical energy delivered during the CCM therapy causes an increase in myocardial contractility of the heart muscle, presumably by increasing intracellular calcium concentration. The CCM increase in contractility in turn increases the stroke volume of the heart contractions, so that more blood is pumped by a subsequent systolic contraction. This counteracts and assists in abating the detected edema. Examples of refractory time periods suitable for initiating delivery of CCM therapy include, by way of example, but not by way of limitation, a time period that is approximately between 1 millisecond and 70 milliseconds following an activation (the CCM energy pulse may, in some examples, extend beyond this refractory time period during which the CCM energy pulse is initiated). In one example, the CCM therapy includes electrical energy pulses, each such pulse having an energy that is, by way of example, but not by way of limitation, approximately between 50 microJoules and 500 microJoules. In one example, the CCM energy pulses are delivered as current pulses, each current pulse having an amplitude that is, by way of example, but not by way of limitation, approximately between 0.5 milliamperes and 20 milliamperes, and each current pulse having a pulsewidth that is, by way of example, but not by way of limitation, approximately between 10 milliseconds and 140 milliseconds. In one example, controller 110 responds to an edema detection by initiating CCM therapy delivered, by way of example, but not by way of limitation, from electrode(s) associated with one or both ventricular heart chambers.

In another example, controller 110 responds to the edema detection by adjusting a parameter associated CCM therapy already being delivered, such as by incrementally increasing the energy (e.g., amplitude and/or pulsewidth) from its programmed value to a higher value until the edema abates or all available increased energy levels have been exhausted.

Figure 8:
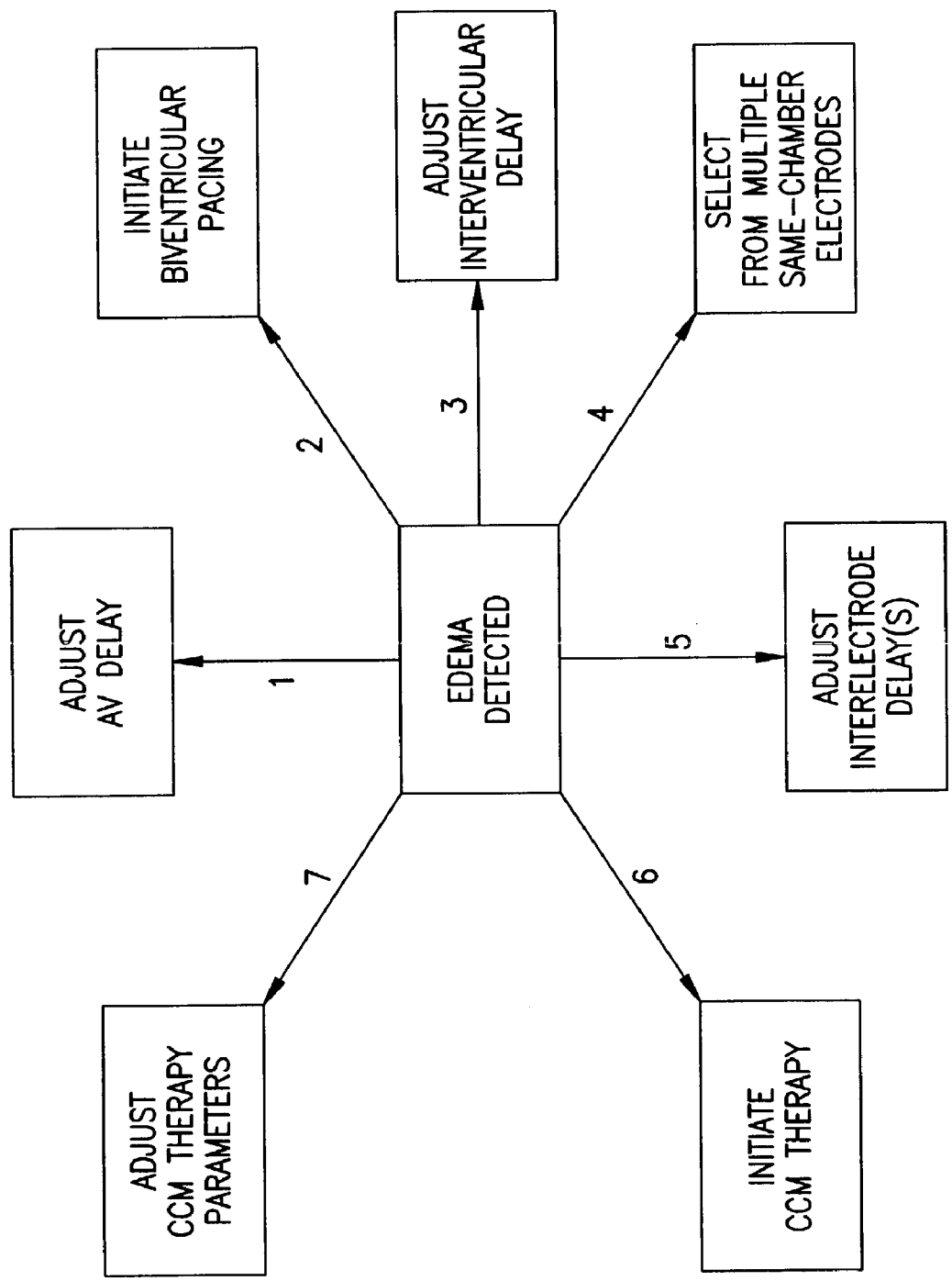
FIG. 8 is a block diagram example in which various responses to a detected edema episode are prioritized.

FIG. 8 is a block diagram example in which various responses to a detected edema episode are prioritized. In this example, controller 110 sequentially attempts the various edema-response measures in the order of priority until the edema abates or all possible responses have been exhausted.

It is to be understood that the above description is intended to be illustrative, and not restrictive. For example, the above-discussed embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

What is claimed is:

1. A method comprising:
    detecting a thoracic impedance of a subject;
    lowpass filtering the thoracic impedance using a cutoff frequency that is approximately between 0.1 Hz and 0.5 Hz to obtain a resulting baseline thoracic impedance;
    obtaining the baseline thoracic impedance at first and second times, the second time delayed from the first time;
    comparing the baseline thoracic impedance at the first time with the baseline thoracic impedance at the second time;
    if the baseline thoracic impedance at the first time is less than the baseline thoracic impedance at the second time by a magnitude that exceeds a predetermined threshold value, then declaring a first condition to exist; and
    initiating or adjusting, in response to the first condition, a cardiac resynchronization therapy that coordinates a spatial nature of a depolarization associated with a heart contraction in at least one heart chamber, the cardiac resynchronization therapy comprising at least one of an interventricular delay and an intraventricular delay.

2. The method of claim 1, in which the initiating or adjusting comprises initiating or adjusting a cardiac contractility modulation therapy that comprises delivering electrical energy to a portion of a heart during a refractory time period of the portion of the heart.

3. The method of claim 1, further comprising:
    detecting a breathing rate of the subject; and
    if the breathing rate exceeds a predetermined threshold value and the first condition was declared to exist, then declaring a second condition to exist.

4. The method of claim 3, further comprising initiating or adjusting a cardiac rhythm management therapy in response to the second condition.

5. The method of claim 4, in which the initiating or adjusting comprises initiating or adjusting a cardiac resynchronization therapy that coordinates a spatial nature of a depolarization associated with a heart contraction in at least one heart chamber.

6. The method of claim 4, in which the initiating or adjusting comprises initiating or adjusting a cardiac contractility modulation therapy that comprises delivering electrical energy to a portion of a heart during a refractory time period of the portion of the heart.

7. A cardiac rhythm management system comprising:
an edema detection circuit to sense a condition correlative to edema in a subject, the edema detection circuit comprising a thoracic impedance detection circuit that comprises:
an averager/lowpass filter, comprising an input to receive a thoracic impedance signal and an output to provide a baseline portion of the thoracic impedance signal;
a delay circuit, comprising an input coupled to the output of the averager/lowpass filter, and comprising an output to provide a delayed baseline portion of the thoracic impedance signal; and
a comparator, comprising a first input coupled to the output of the delay circuit, and comprising a second input coupled to the output of the averager/lowpass filter, and comprising an output providing an edema indicator using a comparison of signals at the first and second inputs of the comparator;
an electrical energy delivery circuit to deliver electrical energy to the subject; and
a controller circuit, coupled to the edema detection circuit to receive the edema indicator, and coupled to the energy delivery circuit to provide a control signal for timing delivery of the electrical energy to the subject, the controller, and in which the controller is configured to initiate or adjust, in response to the edema indicator, a cardiac rhythm management therapy.

8. The system of claim 7, in which the thoracic impedance detection circuit comprises first and second electrodes configured for association with a portion of the subject's thorax.

9. The system of claim 7, in which the averager/lowpass filter comprises an effective cutoff frequency that is between 0.01 Hz and 0.5 Hz.

10. The system of claim 9, in which the cutoff frequency is approximately equal to 0.1 Hz.

11. The system of claim 7, in which the thoracic impedance circuit further comprises a filter circuit to obtain information about the subject's breathing.

12. The system of claim 11, in which the edema detection circuit is configured to provide the edema indicator as determined from both a breathing rate of a subject and a thoracic impedance indication of fluid buildup in the subject's thorax.

13. The system of claim 7, in which the controller comprises a stored interelectrode delay, and in which the controller, in response to the detected edema indicator, is adapted to adjust a value of the interelectrode delay.

14. The system of claim 13, in which the interelectrode delay comprises at least one of an atrioventricular delay, an interventricular delay, and an intraventricular delay.

15. The system of claim 7, in which the controller, in response to the detected edema indicator, is configured to select at least one particular electrode, from a plurality of electrodes differently located in association with a heart of the subject, for subsequent delivery of a contraction-evoking stimulation.

16. The system of claim 15, in which the controller, in response to the detected edema indicator, is configured to select the particular electrode from a plurality of same-chamber electrodes differently located in association with a single chamber of the subject's heart.

17. The system of claim 15, in which the controller, in response to the detected edema indicator, is configured to select the particular electrode from a plurality of electrodes, at least two of which are located in association with different chambers of the subject's heart.

18. The system of claim 7, in which the controller, in response to the detected edema indicator, is configured to initiate or adjust a bi-ventricular pacing therapy to be delivered by the electrical energy circuit.

19. A method comprising:
detecting a thoracic impedance of a subject;
lowpass filtering the thoracic impedance to obtain a resulting lowpass filtered thoracic impedance;
comparing the lowpass filtered thoracic impedance to the thoracic impedance before such lowpass filtering;
if the thoracic impedance before such lowpass filtering is less than the lowpass filtered thoracic impedance by a magnitude that exceeds a predetermined threshold value, then declaring a thoracic fluid accumulation condition to exist.

20. The method of claim 19, further comprising initiating or adjusting a cardiac rhythm management therapy in response to the thoracic fluid accumulation condition.

21. The method of claim 20, in which the initiating or adjusting comprises initiating or adjusting a cardiac resynchronization therapy that coordinates a spatial nature of a depolarization associated with a heart contraction in at least one heart chamber.

22. The method of claim 20, in which the initiating or adjusting comprises initiating or adjusting a cardiac contractility modulation therapy that comprises delivering electrical energy to a portion of a heart during a refractory time period of the portion of the heart.

23. The method of claim 19, further comprising:
detecting a breathing rate of the subject;
if the breathing rate exceeds a predetermined threshold value and the first condition was declared to exist, then declaring a second condition to exist.

24. The method of claim 23, further comprising initiating or adjusting a cardiac rhythm management therapy in response to the second condition.

25. The method of claim 24, in which the initiating or adjusting comprises initiating or adjusting a cardiac resynchronization therapy that coordinates a spatial nature of a depolarization associated with a heart contraction in at least one heart chamber.

26. The method of claim 24, in which the initiating or adjusting comprises initiating or adjusting a cardiac contractility modulation therapy that comprises delivering electrical energy to a portion of a heart during a refractory time period of the portion of the heart.

27. A cardiac rhythm management system comprising:
an edema detection circuit to sense a condition correlative to edema in a subject, the edema detection circuit comprising a thoracic impedance detection circuit that comprises:
an averager/lowpass filter, comprising an input to receive a thoracic impedance signal and an output to provide a baseline portion of the thoracic impedance signal; and
a comparator, comprising a first input coupled to the output of the averager/lowpass filter circuit, and comprising a second input coupled to the input of the averager/lowpass filter, and comprising an output providing an edema indicator using a comparison of signals at the first and second inputs of the comparator;
an electrical energy delivery circuit to deliver electrical energy to the subject; and
a controller circuit, coupled to the edema detection circuit to receive the edema indicator, and coupled to the energy delivery circuit to provide a control signal for timing delivery of the electrical energy to the subject, the controller, and in which the controller is configured to initiate or adjust, in response to the edema indicator, a cardiac rhythm management therapy.

28. The system of claim 27, in which the thoracic impedance detection circuit comprises first and second electrodes configured for association with a portion of the subject's thorax.

29. The system of claim 27, in which the averager/lowpass filter comprises an effective cutoff frequency that is between 0.01 Hz and 0.5 Hz.

30. The system of claim 29, in which the cutoff frequency is approximately equal to 0.1 Hz.

31. The system of claim 27, in which the thoracic impedance circuit further comprises a filter circuit to obtain information about the subject's breathing.

32. The system of claim 31, in which the edema detection circuit is configured to provide the edema indicator as determined from both a breathing rate of a subject and a thoracic impedance indication of fluid buildup in the subject's thorax.

33. The system of claim 27, in which the controller comprises a stored interelectrode delay, and in which the controller, in response to the detected edema indicator, is adapted to adjust a value of the interelectrode delay.

34. The system of claim 33, in which the interelectrode delay comprises at least one of an atrioventricular delay, an interventricular delay, and an intraventricular delay.

35. The system of claim 27, in which the controller, in response to the detected edema indicator, is configured to select at least one particular electrode, from a plurality of electrodes differently located in association with a heart of the subject, for subsequent delivery of a contraction-evoking stimulation.

36. The system of claim 35, in which the controller, in response to the detected edema indicator, is configured to select the particular electrode from a plurality of same-chamber electrodes differently located in association with a single chamber of the subject's heart.

37. The system of claim 35, in which the controller, in response to the detected edema indicator, is configured to select the particular electrode from a plurality of electrodes, at least two of which are located in association with different chambers of the subject's heart.

38. The system of claim 27, in which the controller, in response to the detected edema indicator, is configured to initiate or adjust a bi-ventricular pacing therapy to be delivered by the electrical energy circuit.

39. A method comprising:
sensing, in a subject, a condition correlative to edema; and
initiating or adjusting, in response to the sensing, a cardiac resynchronization therapy that coordinates a spatial nature of a depolarization associated with a heart contraction in at least one heart chamber, the cardiac resynchronization therapy comprising at least one of an interventricular delay and an intraventricular delay.

40. The method of claim 39, in which the sensing comprises detecting a change in a baseline thoracic impedance associated with fluid buildup in a portion of a thorax of the subject.

41. The method of claim 40, in which the sensing comprises detecting a decrease in the baseline thoracic impedance associated with fluid buildup in the portion of the thorax of the subject.

42. The method of claim 41, in which the baseline portion of the thoracic impedance is less than or equal to a cutoff frequency value that is between 0.01 Hz and 0.5 Hz inclusive.

43. The method of claim 42, in which the cutoff frequency value is approximately 0.1 Hz.

44. The method of claim 40, in which the sensing also comprises detecting an increase in a rate of breathing of the subject.

45. The method of claim 44, in which the detecting the increase in the breathing rate comprises sensing the breathing of the subject from a portion of the thoracic impedance that is approximately between 0.05 Hz and 2.0 Hz inclusive.

46. The method of claim 39, in which the initiating or adjusting the cardiac resynchronization therapy comprises selecting an interelectrode delay value, for subsequent delivery of contraction-evoking stimulations occurring during a single cardiac cycle.

47. A method comprising:
sensing, in a subject, a condition correlative to edema; and
initiating or adjusting, in response to the sensing, a cardiac resynchronization therapy that coordinates a spatial nature of a depolarization associated with a heart contraction in at least one heart chamber, in which the initiating or adjusting the cardiac resynchronization therapy comprises selecting at least one particular electrode, from a plurality of electrodes differently located in association with a heart of the subject, for subsequent delivery of a contraction-evoking stimulation.

48. The method of claim 47, in which selecting the interelectrode delay value comprises selecting at least one of an atrioventricular delay value, an interventricular delay value, and an intraventricular delay value.

49. The method of claim 47, in which the selecting the particular electrode comprises selecting the particular electrode from a plurality of same-chamber electrodes differently located in association with a single chamber of the subject's heart.

50. The method of claim 47, in which the selecting the particular electrode comprises selecting the particular electrode from a plurality of electrodes, at least two of which are located in association with different chambers of the subject's heart.

51. A method comprising:
sensing, in a subject, a condition correlative to edema; and
initiating or adjusting, in response to the sensing, a cardiac resynchronization therapy that coordinates a spatial nature of a depolarization associated with a heart contraction in at least one heart chamber, in which the initiating or adjusting the cardiac resynchronization therapy comprises initiating or adjusting biventricular pacing.

52. The method of claim 51, in which the initiating or adjusting the cardiac resynchronization therapy comprises initiating biventricular pacing.

53. A method comprising:
sensing, in a subject, a condition correlative to edema; and
initiating or adjusting, in response to the sensing, a cardiac resynchronization therapy that comprises at least one of an interventricular delay and an intraventricular delay.

54. The method of claim 53, in which the sensing comprises detecting a change in a baseline thoracic impedance associated with fluid buildup in a portion of a thorax of the subject.

55. The method of claim 54, in which the sensing comprises detecting a decrease in the baseline thoracic impedance associated with fluid buildup in the portion of the thorax of the subject.

56. The method of claim 55, in which the baseline portion of the thoracic impedance is less than or equal to a cutoff frequency value that is between 0.01 Hz and 0.5 Hz inclusive.

57. The method of claim 56, in which the cutoff frequency value is approximately 0.1 Hz.

58. The method of claim 54, in which the sensing also comprises detecting an increase in a rate of breathing of the subject.

59. The method of claim 58, in which the detecting the increase in the breathing rate comprises sensing the breathing of the subject from a portion of the thoracic impedance that is approximately between 0.05 Hz and 2.0 Hz inclusive.

60. The method of claim 53, in which the initiating or adjusting further comprises providing a non-contraction-evoking stimulus to a location of a heart of the subject during a refractory period of the heart location.

61. The method of claim 60, in which the refractory period follows a paced or sensed contraction of the heart location.

62. A method comprising:
sensing, in a subject, a condition correlative to edema; and
selecting, in response to the sensing, a cardiac rhythm management therapy from a prioritized list of therapies.

63. The method of claim 62, in which the sensing comprises detecting a change in a baseline thoracic impedance associated with fluid buildup in a portion of a thorax of the subject.

64. The method of claim 63, in which the sensing comprises detecting a decrease in the baseline thoracic impedance associated with fluid buildup in the portion of the thorax of the subject.

65. The method of claim 64, in which the baseline portion of the thoracic impedance is less than or equal to a cutoff frequency value that is between 0.01 Hz and 0.5 Hz inclusive.

66. The method of claim 65, in which the cutoff frequency value is approximately 0.1 Hz.

67. The method of claim 63, in which the sensing also comprises detecting an increase in a rate of breathing of the subject.

68. The method of claim 67, in which the detecting the increase in the breathing rate comprises sensing the breathing of the subject from a portion of the thoracic impedance that is approximately between 0.05 Hz and 2.0 Hz inclusive.

69. The method of claim 62, comprising initiating/adjusting a cardiac resynchronization therapy, selecting an interelectrode delay value, for subsequent delivery of contraction-evoking stimulations occurring during a single cardiac cycle.

70. The method of claim 62, comprising initiating/adjusting a cardiac resynchronization therapy, including selecting at least one particular electrode, from a plurality of electrodes differently located in association with a heart of the subject, for subsequent delivery of a contraction-evoking stimulation.

71. The method of claim 70, in which selecting the interelectrode delay value comprises selecting at least one of an atrioventricular delay value, an interventricular delay value, and an intraventricular delay value.

72. The method of claim 70, in which the selecting the particular electrode comprises selecting the particular electrode from a plurality of same-chamber electrodes differently located in association with a single chamber of the subject's heart.

73. The method of claim 70, in which the selecting the particular electrode comprises selecting the particular electrode from a plurality of electrodes, at least two of which are located in association with different chambers of the subject's heart.

74. The method of claim 62, comprising initiating/adjusting a cardiac contractility modulation therapy, including providing a non-contraction-evoking stimulus to a location of a heart of the subject during a refractory period of the heart location.

75. The method of claim 74, in which the refractory period follows a paced or sensed contraction of the heart location.

76. The method of claim 62, in which the selecting comprises adjusting an AV delay before initiating a biventricular pacing.

77. The method of claim 62, in which the selecting comprises adjusting an AV delay before adjusting an interventricular delay.

78. The method of claim 62, in which the selecting comprises adjusting an AV delay before selecting at least one particular electrode from among multiple same-chamber electrodes.

79. The method of claim 62, in which the selecting comprises adjusting an AV delay before adjusting one or more interelectrode delays.

80. The method of claim 62, in which the selecting comprises adjusting an AV delay before initiating a cardiac contractility modulation therapy.

81. The method of claim 62, in which the selecting comprises adjusting an AV delay before adjusting one or more cardiac contractility modulation therapy parameters.

82. The method of claim 62, in which the selecting comprises initiating biventricular pacing before adjusting an interventricular delay.

83. The method of claim 62, in which the selecting comprises initiating biventricular pacing before selecting at least one particular electrode from among multiple same-chamber electrodes.

84. The method of claim 62, in which the selecting comprises initiating biventricular pacing before adjusting one or more interelectrode delays.

85. The method of claim 62, in which the selecting comprises initiating biventricular pacing before initiating cardiac contractility modulation therapy.

86. The method of claim 62, in which the selecting comprises initiating biventricular pacing before adjusting one or more cardiac contractility modulation parameters.

87. The method of claim 62, in which the selecting comprises adjusting an interventricular delay before selecting at least one particular electrode from among multiple same-chamber electrodes.

88. The method of claim 62, in which the selecting comprises adjusting an interventricular delay before adjusting one or more interelectrode delays.

89. The method of claim 62, in which the selecting comprises adjusting an interventricular delay before initiating a cardiac contractility modulation therapy.

90. The method of claim 62, in which the selecting comprises adjusting an interventricular delay before adjusting one or more cardiac contractility modulation parameters.

91. The method of claim 62, in which the selecting comprises selecting at least one particular electrode from among multiple same-chamber electrodes before adjusting one or more interelectrode delays.

92. The method of claim 62, in which the selecting comprises selecting at least one particular electrode from among multiple same-chamber electrodes before initiating cardiac contractility modulation therapy.

93. The method of claim 62, in which the selecting comprises selecting at least one particular electrode from among multiple same-chamber electrodes before adjusting one or more cardiac contractility modulation parameters.

94. The method of claim 62, in which the selecting comprises adjusting one or more interelectrode delays before initiating a cardiac contractility modulation therapy.

95. The method of claim 62, in which the selecting comprises adjusting one or more interelectrode delays before adjusting one or more cardiac contractility modulation parameters.

96. The method of claim 62, in which the selecting comprises using a prioritization between cardiac rhythm management therapies in which adjusting an AV delay is prioritized higher than initiating biventricular pacing, which is prioritized higher than adjusting an interventricular delay, which is prioritized higher than selecting at least one particular electrode from among multiple same-chamber electrodes, which is prioritized higher than adjusting one or more interelectrode delays, which is prioritized higher than initiating a cardiac contractility modulation therapy, which is prioritized higher than adjusting one or more cardiac contractility modulation parameters.

97. A cardiac rhythm management system comprising:
an edema detection circuit to sense a condition correlative to edema in a subject;
an electrical energy delivery circuit to deliver electrical energy to the subject; and
a controller circuit, coupled to the edema detection circuit to receive a detected edema indicator, and coupled to the energy delivery circuit to provide a control signal for timing delivery of the electrical energy to the subject, the controller comprising a cardiac resynchronization therapy parameter, and in which the controller is configured to initiate or adjust, in response to the detected edema indicator, a cardiac resynchronization therapy that coordinates a spatial nature of a depolarization associated with a heart contraction in at least one heart chamber, the cardiac resynchronization therapy comprising at least one of an interventricular delay and an intraventricular delay.

98. The system of claim 97, in which the edema detection circuit comprises a thoracic impedance detection circuit.

99. The system of claim 98, in which the thoracic impedance detection circuit comprises first and second electrodes configured for association with a portion of the subject's thorax.

100. The system of claim 99, in which the thoracic impedance detection circuit further comprises an averager/lowpass filter to obtain a baseline portion of the thoracic impedance signal associated with the condition correlative to edema.

101. The system of claim 100, in which the averager/lowpass filter comprises an effective cutoff frequency that is between 0.01 Hz and 0.5 Hz.

102. The system of claim 101, in which the cutoff frequency is approximately equal to 0.1 Hz.

103. The system of claim 99, in which the thoracic impedance circuit further comprises a filter circuit to obtain information about the subject's breathing.

104. The system of claim 97, in which the edema detection circuit provides the condition correlative to edema as determined from both a breathing rate of a subject and a thoracic impedance indication of fluid buildup in the subject's thorax.

105. The system of claim 97, in which the controller comprises a stored interelectrode delay, and in which the controller, in response to the detected edema indicator, adjusts a value of the interelectrode delay.

106. The system of claim 105, in which the interelectrode delay comprises at least one of an atrioventricular delay, an interventricular delay, and an intraventricular delay.

107. A cardiac rhythm management system comprising:
an edema detection circuit to sense a condition correlative to edema in a subject;
an electrical energy delivery circuit to deliver electrical energy to the subject; and
a controller circuit, coupled to the edema detection circuit to receive a detected edema indicator, and coupled to the energy delivery circuit to provide a control signal for timing delivery of the electrical energy to the subject, the controller comprising a cardiac resynchronization therapy parameter, and in which the controller is configured to initiate or adjust, in response to the detected edema indicator, a cardiac resynchronization therapy that coordinates a spatial nature of a depolarization associated with a heart contraction in at least one heart chamber, in which the controller, in response to the detected edema indicator, selects at least one particular electrode, from a plurality of electrodes differently located in association with a heart of the subject, for subsequent delivery of a contraction-evoking stimulation.

108. The system of claim 107, in which the controller, in response to the detected edema indicator, selects the particular electrode from a plurality of same-chamber electrodes differently located in association with a single chamber of the subject's heart.

109. The system of claim 107, in which the controller, in response to the detected edema indicator, selects the particular electrode from a plurality of electrodes, at least two of which are located in association with different chambers of the subject's heart.

110. A cardiac rhythm management system comprising:
an edema detection circuit to sense a condition correlative to edema in a subject;
an electrical energy delivery circuit to deliver electrical energy to the subject; and
a controller circuit, coupled to the edema detection circuit to receive a detected edema indicator, and coupled to the energy delivery circuit to provide a control signal for timing delivery of the electrical energy to the subject, the controller comprising a cardiac resynchronization therapy parameter, and in which the controller is configured to initiate or adjust, in response to the detected edema indicator, a cardiac resynchronization therapy that coordinates a spatial nature of a depolarization associated with a heart contraction in at least one heart chamber, in which the controller, in response to the detected edema indicator, is configured to initiate or adjust a bi-ventricular pacing therapy to be delivered by the electrical energy circuit.

111. A cardiac rhythm management system comprising:
an edema detection circuit to sense a condition correlative to edema in a subject;
an electrical energy delivery circuit to deliver electrical energy to the subject; and a controller circuit, coupled to the edema detection circuit to receive a detected edema indicator, and coupled to the energy delivery circuit to provide a control signal for timing delivery of the electrical energy to the subject, the controller comprising a cardiac contractility therapy mode, and in which the controller is configured to initiate or adjust, in response to the detected edema indicator, a cardiac resynchronization therapy that comprises at least one of an interventricular delay and an intraventricular delay.

112. The system of claim 111, in which the edema detection circuit comprises a thoracic impedance detection circuit.

113. The system of claim 112, in which the thoracic impedance detection circuit comprises first and second electrodes configured for association with a portion of the subject's thorax.

114. The system of claim 113, in which the thoracic impedance detection circuit further comprises an averager/lowpass filter to obtain a baseline portion of the thoracic impedance signal associated with the condition correlative to edema.

115. The system of claim 114, in which the averager/lowpass filter comprises an effective cutoff frequency that is between 0.01 Hz and 0.5 Hz.

116. The system of claim 115, in which the cutoff frequency is approximately equal to 0.1 Hz.

117. The system of claim 113, in which the thoracic impedance circuit further comprises a filter circuit to obtain information about the subject's breathing.

118. The system of claim 111, in which the edema detection circuit provides the condition correlative to edema as determined from both a breathing rate of a subject and a thoracic impedance indication of fluid buildup in the subject's thorax.

* * * * *

UNITED STATES PATENT AND TRADEMARK OFFICE
CERTIFICATE OF CORRECTION

| | | |
|---|---|---|
| PATENT NO. | : 7,177,681 B2 | Page 1 of 1 |
| APPLICATION NO. | : 10/411795 | |
| DATED | : February 13, 2007 | |
| INVENTOR(S) | : Zhu et al. | |

It is certified that error appears in the above-identified patent and that said Letters Patent is hereby corrected as shown below:

In column 13, line 52, in Claim 69, before "selecting" insert -- including --.

Signed and Sealed this

Fifteenth Day of May, 2007

JON W. DUDAS
*Director of the United States Patent and Trademark Office*